(12) United States Patent
Warashina et al.

(10) Patent No.: US 11,717,487 B2
(45) Date of Patent: *Aug. 8, 2023

(54) ENTERIC COATING COMPOSITION, SOLID PREPARATION AND METHOD FOR PRODUCING SOLID PREPARATION

(71) Applicant: Shin-Etsu Chemical Co., Ltd., Tokyo (JP)

(72) Inventors: Shogo Warashina, Niigata (JP); Yasuyuki Hirama, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 129 days.

This patent is subject to a terminal disclaimer.

(21) Appl. No.: 16/837,831

(22) Filed: Apr. 1, 2020

(65) Prior Publication Data

US 2020/0315977 A1 Oct. 8, 2020

(30) Foreign Application Priority Data

Apr. 4, 2019 (JP) .................................. 2019-071880

(51) Int. Cl.
| | |
|---|---|
| *A61K 9/50* | (2006.01) |
| *A61K 9/28* | (2006.01) |
| *A61K 9/48* | (2006.01) |
| *A61K 47/10* | (2017.01) |

(52) U.S. Cl.
CPC ............ *A61K 9/5047* (2013.01); *A61K 47/10* (2013.01)

(58) Field of Classification Search
None
See application file for complete search history.

(56) References Cited

U.S. PATENT DOCUMENTS

| | | | | |
|---|---|---|---|---|
| 5,508,276 | A * | 4/1996 | Anderson | A61P 25/26 424/463 |
| 10,493,161 | B2 * | 12/2019 | Warashina | A61K 9/146 |
| 11,141,381 | B2 * | 10/2021 | Maruyama | B29C 41/14 |
| 2012/0251588 | A1 | 10/2012 | Fukasawa et al. | |
| 2014/0357681 | A1 | 12/2014 | Warashina et al. | |
| 2016/0136283 | A1 | 5/2016 | Warashina et al. | |
| 2017/0283514 | A1 | 10/2017 | Matsubara et al. | |
| 2018/0015045 | A1 * | 1/2018 | Maruyama | A61K 9/4816 |

FOREIGN PATENT DOCUMENTS

| | | |
|---|---|---|
| JP | 56-127322 A | 6/1981 |
| JP | 2016-098179 A | 5/2016 |
| JP | 2017-186331 A | 10/2017 |
| WO | 2018170062 A1 | 9/2018 |

OTHER PUBLICATIONS

Chen, R., et al. "Hypromellose Acetate Succinate" in Handbook of Pharmaceutical Excipients. Pharmaceutical Press and American Pharmacists Association 2009 (6th Edition) 330-332. (Year: 2009).*
"Hypromellose Acetate Succinate" in: "Handbook of Pharmaceutical Excipients", Pharmaceutical Press, London, XP055716974, pp. 330-332, p. 330, paragraph 6; p. 331, paragraph 10; R.Chen, et al., Jan. 1, 2009.
European Search Report for Application No. 20166676.5, dated Jul. 31, 2020.
Office Action for Japanese Application No. 2019-071880 dispatched Dec. 22, 2021.
The Japanese Pharmacopoeia, Seventeenth Edition, dated Apr. 1, 2016.
Communication Pursuant to Article 94(3) EPC for EP Application No. 20 166 676.5, dated Mar. 31, 2023 (6 pages).
"Aqua Solve and Aqua Solve AS—Hydroxypropylmethylcellulose Acetate Succinate—Physical and Chemical Properties Handbook". Jan. 2013, Retrieved from the Internet: URL:http://www.ashland.com/Ashland/Static/Documents/ASI/PC_12624_AquaSolve_AS_Handbook.pdf on Apr. 29, 2014 (16 pages).

* cited by examiner

*Primary Examiner* — Bethany P Barham
*Assistant Examiner* — Peter Anthopolos
(74) *Attorney, Agent, or Firm* — Rimon, P.C.

(57) ABSTRACT

There are provided an enteric coating composition having an excellent film-forming property, being capable of forming a film at a lower temperature than conventional compositions, and/or being capable of avoiding decomposition of a drug due to a high temperature and operational troubles due to or nozzle clogging; and others. More specifically, there are provided an enteric coating composition containing hypromellose acetate succinate having a molar substitution of hydroxypropoxy groups of 0.40 or more, and water; a method for producing a solid preparation including steps of coating a drug-containing core with the enteric coating composition to obtain a coating layer, and drying the coating layer; and a solid preparation containing a drug-containing core, and a coating layer directly or indirectly on the core, the coating layer containing a hypromellose acetate succinate having a molar substitution of hydroxypropoxy groups of 0.40 or more.

7 Claims, No Drawings

ENTERIC COATING COMPOSITION, SOLID PREPARATION AND METHOD FOR PRODUCING SOLID PREPARATION

CROSS REFERENCE TO RELATED APPLICATIONS

This application claims the benefit of priority from Japanese Patent Application No. 2019-071880, filed on Apr. 4, 2019, the contents of which are incorporated by reference.

BACKGROUND OF THE INVENTION

1. Field of the Invention

The invention relates to an enteric coating composition which is an aqueous dispersion comprising hypromellose acetate succinate and water; and the applications of the composition.

2. Related Art

Drugs used in pharmaceutical applications include those that degrade under acidic conditions. When such drugs are administered, they decompose in the stomach having acidic conditions before reaching an absorption site of small intestine. Thus, it is difficult to exert the effect of the drug administration. Acid-resistant dosage forms are widely used to deliver such drugs into the intestine. For example, coating with an enteric coating composition is known as a technique for coating tablets, granules and powders with a polymer to protect them from the decomposition in the stomach and to achieve rapid dissolution in the intestine.

Examples of the polymer used as an enteric base material include hypromellose acetate succinate ester (hereinafter also referred to as "HPMCAS") having two substituents of methoxy group ($-OCH_3$) and hydroxypropoxy group ($-OC_3H_6OH$) as ether structures and two substituents of acetyl group ($-COCH_3$) and succinyl group ($-COC_2H_4COOH$) as ester structures in the cellulose skeleton.

The content of each substituent of HPMCAS listed in the Japanese Pharmacopoeia 17th Edition is specified as follows (see "Hypromellose Acetate Succinate Ester" in the Official Monograph of the Japanese Pharmacopoeia 17th Edition).

TABLE 1

| | content (% by mass) | molar substitution (MS) or degree of substitution (DS) |
|---|---|---|
| methoxy group | 12.0~28.0 | 0.73~2.83 |
| hydroxypropoxy group | 4.0~23.0 | 0.10~1.90 |
| acetyl group | 2.0~16.0 | 0.09~2.30 |
| succinyl group | 4.0~28.0 | 0.08~1.78 |

\* The molar substitution is an average molar number of substituents added per anhydroglucose unit, and the degree of substitution is an average number of substituents added per anhydroglucose unit.

As an enteric coating composition which is an aqueous dispersion containing HPMCAS, there has been proposed, in JPS 56-127322A, an enteric coating composition for a solid preparation in which HPMCAS having an average particle size of 10 μm (with the largest particle size of 30 μm) is dispersed in an aqueous medium containing triethyl citrate as a plasticizer

SUMMARY OF THE INVENTION

However, in JPS 56-127322A, 25 parts by mass of triethyl citrate as a plasticizer relative to 100 parts by weight of HPMCAS having a molar substitution (MS) of hydroxypropoxy groups of 0.27, a degree of substitution (DS) of methoxy groups of 1.85, a degree of substitution (DS) of acetyl groups of 0.51 and a degree of substitution (DS) of succinyl groups of 0.28 is used. This is to form a satisfactory enteric coating film, but a large amount of plasticizer may cause agglomeration of the HPMCAS during preparation of the aqueous dispersion or clogging of the nozzle during coating. Thus, there is room for improvement in maintaining the stability of enteric coating film and the enteric properties. On the other hand, reducing the amount of the plasticizer requires heating at a high temperature to form a film, which is undesirable from the standpoint of drug stability.

Thus, there is room for improvement in the enteric coating composition containing HPMCAS. The invention has been made in view of the above-mentioned circumstances. An object thereof is to provide an enteric coating composition having an excellent film-forming property, being capable of forming a film at a lower temperature than conventional compositions and/or being capable of avoiding the decomposition of a drug due to a high temperature or a trouble in operation due to clogging of the nozzle.

As a result of intensive studies to solve the above-mentioned problems, the inventors have found that the film-forming property of the enteric coating composition can be improved by setting a molar substitution of hydroxypropoxy groups to a specified range in the HPMCAS, and the invention has been made.

In one aspect of the invention, there is provided an enteric coating composition comprising hypromellose acetate succinate having a molar substitution of hydroxypropoxy groups of 0.40 or more, and water.

In another aspect of the invention, there is provided a method for preparing a solid preparation comprising steps of: coating a drug-containing core with the enteric coating composition to obtain a coating layer, and drying the coating layer.

In still another aspect of the invention, there is provided a solid preparation comprising a drug-containing core, and a coating layer directly or indirectly on the core, the coating layer comprising hypromellose acetate succinate ester having a molar substitution of hydroxypropoxy groups of 0.40 or more.

According to the invention, since the film can be formed at a temperature lower than conventional and/or in addition of none or a smaller amount of plasticizer, decomposition of the drug due to a high temperature and/or operational troubles due to nozzle clogging can be avoided.

DETAILED DESCRIPTION OF THE PREFERRED EMBODIMENTS

An enteric coating composition, which is an aqueous dispersion and comprises HPMCAS having a molar substitution of hydroxypropoxy groups of 0.40 or more and water, will be described. Regarding the aqueous dispersion, a portion of the HPMCAS may be dissolved in the aqueous dispersion.

The molar substitution of hydroxypropoxy groups in the HPMCAS is 0.40 or more, preferably 0.42 or more, more preferably 0.50 or more, still more preferably 0.55 or more, and particularly preferably 0.60 or more. When the molar substitution (MS) of hydroxypropoxy groups is less than 0.40, higher temperatures are required to form a film, and/or a certain amount of a plasticizer has to be added to the enteric coating composition for obtaining the film-forming property. As a result, the agglomeration of the HPMCAS may increase, handling may be deteriorated during coating, or the stability after coating may be deteriorated.

The molar substitution (MS) of hydroxypropoxy groups in the HPMCAS is preferably 1.00 or less, more preferably 0.90 or less, still more preferably 0.85 or less, and particularly preferably 0.80 or less, from the standpoint of the productivity of the HPMCAS.

More particularly, the molar substitution (MS) of hydroxypropoxy groups in the HPMCAS is preferably from 0.40 to 1.00, more preferably from 0.42 to 0.90, still more preferably from 0.50 to 0.85, further still more preferably from 0.55 to 0.85, particularly preferably from 0.60 to 0.80.

The degree of substitution (DS) of methoxy groups in the HPMCAS is not particularly limited. It is preferably 0.70 to 2.50, more preferably 1.00 to 2.20, and still more preferably 1.40 to 1.95, from the standpoint of the productivity of the HPMCAS and the film strength.

The degree of substitution (DS) of acetyl groups in the HPMCAS is not particularly limited. It is preferably 0.10 to 2.50, more preferably 0.10 to 1.00, and still more preferably 0.40 to 0.96, from the standpoint of acid resistance and an enteric property.

The degree of substitution (DS) of succinyl groups in the HPMCAS is not particularly limited. It is preferably 0.10 to 2.50, more preferably 0.10 to 1.00, still more preferably 0.10 to 0.60, and particularly preferably 0.15 to 0.45, from the standpoint of acid resistance and an enteric property.

The contents of hydroxypropoxy and methoxy groups in HPMCAS may be obtained by the methods described in the Official Monograph "Hypromellose" of the Japanese Pharmacopoeia 17th Edition.

The contents of acetyl and succinyl groups may be obtained by the method described in the Official Monograph "Hypromellose Acetate Succinate Ester" of the Japanese Pharmacopoeia 17th Edition.

A ratio of the degree of substitution of acetyl groups to the molar substitution of hydroxypropoxy groups (degree of substitution of acetyl groups/molar substitution of hydroxypropoxy groups) in the HPMCAS is preferably more than 0 and not more than 2.50, more preferably from 0.40 to 2.00, still more preferably from 0.50 to 1.60, particularly preferably from 0.60 to 1.30, and most preferably from 0.70 to 1.00, from the standpoint of film formation temperature and acid resistance.

A ratio of the degree of substitution of acetyl groups to the degree of substitution of succinyl groups (degree of substitution of acetyl groups/degree of substitution of succinyl groups) in the HPMCAS is preferably more than 0 and not more than 4.5, more preferably 0.50 to 4.00, still more preferably 0.50 to 3.00, and particularly preferably 0.50 to 2.50, from the standpoint of film formation temperature.

Preferable HPMCAS can be obtained by combining the above-mentioned ranges of the molar substitution (MS) of hydroxypropoxy groups, the degree of substitution (DS) of methoxy groups, the degree of substitution (DS) of acetyl groups, and the degree of substitution (DS) of succinyl groups. More preferable HPMCAS satisfies either one of the range of the ratio of the degree of substitution of acetyl groups to the molar substitution of hydroxypropoxy groups and the range of the ratio of the degree of substitution of acetyl groups to the degree of substitution of succinyl groups, and it is still more preferable that the preferred HPMCAS satisfy both of the ranges.

For example, preferable HPMCAS has the molar substitution (MS) of hydroxypropoxy groups of 0.40 to 1.00, the degree of substitution (DS) of methoxy groups of 0.70 to 2.50, the degree of substitution (DS) of acetyl groups of 0.10 to 2.50 and the degree of substitution (DS) of succinyl groups of 0.10 to 2.50. More preferable HPMCAS has a ratio of the degree of substitution of acetyl groups to the molar substitution of hydroxypropoxy groups of more than 0 and not more than 2.5 and/or a ratio of the degree of substitution of acetyl groups to the degree of substitution of succinyl group of more than 0 and not more than 4.5. Still more preferable HPMCAS has the molar substitution (MS) of hydroxypropoxy groups of 0.40 to 0.90, the degree of substitution (DS) of methoxy groups of 1.40 to 1.95, the degree of substitution (DS) of acetyl groups of 0.40 to 0.96, and the degree of substitution (DS) of succinyl groups of 0.15 to 0.45. It is further still more preferable that said still more preferable HPMCAS have a ratio of the degree of substitution of acetyl groups to the molar substitution of hydroxypropoxy groups of 0.70 to 1.00 and/or a ratio of the degree of substitution of acetyl groups to the degree of substitution of succinyl groups is 0.50 to 4.00.

The degree of substitution or the molar substitution of each type of substituents can be converted from the content % of each type of substituents.

Specifically, the conversion can be performed by the following equations.

In the equations, "Da" denotes dalton, AGU denotes an anhydroglucose unit, "% HPO" denotes the content of hydroxypropoxy groups, "% MeO" denotes the content of methoxy groups, "% Ac" denotes the content of acetyl groups, "% Suc" denotes the content of succinyl groups, and "Fw" denotes the average molecular weight per glucose unit of HPMCAS. In addition, "M(MeO)" is the molecular weight of (OCH$_3$) and assigned to be 31.03 Da, "M(HPO)" is the molecular weight of the hydroxypropoxy group OCH$_2$CH(OH)CH$_3$ and assigned to be 75.09 Da, M(Ac) is the molecular weight of the acetyl group COCH$_3$ and assigned to be 43.04 Da, M(Suc) is the molecular weight of the succinyl group and assigned to be 101.08 Da, M(AGU) is the molecular weight per glucose unit in cellulose and assigned to be 162.14 Da, M(OH) is the molecular weight of OH and assigned to be 17.008 Da, M(H) is the atomic weight of H and assigned to be 1.008 Da.

$$MS(HPO)=\{\% \ HPO/M(HPO)\}*Fw$$

$$DS(Me)=\{\% \ MeO/M(MeO)\}*Fw$$

$$DS(Ac)=\{\% \ Ac/M(Ac)\}*Fw$$

$$DS(Suc)=\{\% \ Suc/M(Suc)\}*Fw$$

$$Fw=(M(AGU)*100)/G$$

$$G=100-[\% \ MeO*\{M(MeO)-M(OH)\}/M(MeO)]-[\% \ HPO*\{M(HPO)-M(OH)\}/M(HPO)]-[\% \ Ac*\{M(Ac)-M(H)\}/M(Ac)]-$$

$$[\% \ Suc*\{M(Suc)-M(H)\}/M(Suc)].$$

The viscosity at 20° C. of 2% by mass of HPMCAS in a dilute aqueous sodium hydroxide solution (a sodium hydroxide concentration of 0.1 mol/L) is preferably 1.10 to 20.00 mPa·s, more preferably 1.50 to 4.00 mPa·s, and still more preferably 2.40 to 3.60 mPa·s, from the standpoint of manufacturability and film strength.

The viscosity at 20° C. of 2% by mass solution of HPMCAS in a dilute aqueous sodium hydroxide solution (a sodium hydroxide concentration of 0.1 mol/L) can be measured using a Ubbelohde-type viscometer in accordance with the "Viscosity Determination" of the "General Tests" of the Japanese Pharmacopoeia 17th Edition, as described in the "Viscosity" of the "Hypromellose Acetate Succinate Ester".

The volume-average particle size of the HPMCAS can be measured by a dry laser-diffraction particle size distribution measurement apparatus.

The volume-average particle size is calculated using the equation $\{\Sigma(nD^3)/\Sigma n\}/3$ as described, for example, in "Kaitei-Zoho Funtai Bussei Zukan (Powder Properties Illustration Revised and Enlarged Edition" edited by the Society of Powder Technology, Japan and the Association of Powder Process Industry and Engineers, Japan; Nikkei Technical Library, 1985, p. 88. In the equation, D denotes a diameter (or size) of a particle, n denotes the number of particles having said diameter, and $\Sigma n$ denotes the total number of particles.

The dry laser-diffraction particle size distribution measurement apparatus is an apparatus for spraying a powder sample with compressed air, irradiating the powder sample with a laser beam, and measuring the volume-average particle size by the diffraction strength of the powder sample. Examples of the apparatus include a Mastersizer manufactured by Malvern Corporation of the United Kingdom, a HELOS apparatus manufactured by Sympatec Corporation of Germany. The measurement conditions will be described in detail in Examples.

In terms of the volume particle size, $D_{10}$ means a particle size corresponding to 10% of the cumulative particle size distribution, $D_{50}$ means a particle size corresponding to 50% of the cumulative particle size distribution, and $D_{90}$ means a particle size corresponding to 90% of the cumulative particle size distribution. The particle size ($D_{50}$) of the HPMCAS may be used as a volume-average particle size of the HPMCAS.

The particle size ($D_{10}$) of the HPMCAS is preferably 10.0 μm or less, more preferably 0.1 to 5.0 μm, still more preferably 0.2 to 3.0 μm, and particularly preferably 0.5 to 2.5 μm, from the standpoint of the film-forming property and formation of a dense film.

The particle size ($D_{50}$) of the HPMCAS is preferably 30 μm or less, more preferably 1 to 20 μm, still more preferably 2 to 15 μm, and particularly preferably 3 to 10 μm, from the standpoint of the film-forming property and formation of a dense film.

The particle size ($D_{90}$) of the HPMCAS is preferably 40 μm or less, more preferably 2 to 30 μm, and still more preferably 3 to 20 μm, from the standpoint of the film-forming property and formation of a dense film.

HPMCAS having a molar substitution of hydroxypropoxy groups of 0.40 or more may be produced by using hypromellose (also called hydroxypropyl methyl cellulose and hereinafter also referred to as "HPMC") having a molar substitution (MS) of hydroxypropoxy groups of 0.40 or more.

The molar substitution (MS) of hydroxypropoxy groups in the HPMC is preferably 0.40 or more, more preferably 0.40 to 1.00, from the standpoint of the molar substitution (MS) of the HPMCAS to be synthesized. More specifically, it is the same as the above description with respect to the molar substitution (MS) of hydroxypropoxy groups of the HPMCAS. The degree of substitution (DS) of methoxy groups in the HPMC is the same as the above description with respect to the degree of substitution (DS) of methoxy groups in the HPMCAS to be synthesized, and is preferably 0.70 to 2.50, more preferably 1.00 to 2.20, and still more preferably 1.40 to 1.95.

The molar substitution (MS) of hydroxypropoxy groups and the degree of substitution (DS) of methoxy groups in the HPMC may be converted from the values calculated by the method described in the Official Monograph "Hypromellose" of the Japanese Pharmacopoeia 17th Edition.

The degree of substitution (DS) of HPMC refers to an average number of methoxy groups per anhydroglucose unit, and the molar substitution (MS) of HPMC refers to an average molar number of hydroxypropoxy groups per anhydroglucose unit.

The HPMCAS may be produced by esterifying the HPMC by a known method, and the HPMC may be produced by a known method. For example, HPMC as a starting material is dissolved in glacial acetic acid, subjected to additions of acetic anhydride and succinic anhydride as esterifying agents and sodium acetate as a reaction catalyst, and heated at 60 to 110° C. for 2 to 25 hours to obtain a reaction product mixture. After completion of the reaction, a large amount of water is added to the reaction product mixture to obtain a suspension in which HPMCAS is precipitated. The precipitated HPMCAS is washed with purified water or the like, dried, and sieved through a sieve to obtain synthesized HPMCAS. The obtained HPMCAS may be pulverized and subjected to optional sieving to obtain HPMCAS having a target average particle size.

The pulverization of the HPMCAS is not particularly limited, and may be dry pulverization or wet pulverization.

The pulverizer is not particularly limited as long as it is capable of pulverizing an object to a desired particle size. Examples of the pulverizer include an airflow type impact pulverizer, an impact pulverizer, a medium agitation pulverizer, a container driving medium pulverizer, and a compaction pulverizer. The pulverizer is preferably an airflow type impact pulverizer, an impact pulverizer, and a medium agitation pulverizer from the standpoint of preventing the product temperature from increasing in consideration of low softening temperature of HPMCAS. Examples of the airflow type impact pulverizer include a jet mill, examples of the impact pulverizer include a knife mill and a pin mill, and examples of the medium agitation pulverizer include a bead mill.

HPMCAS is dispersed in water in the enteric coating composition. Examples of the water include ion-exchanged water, and pure water. The pure water is preferable from the standpoint of impurities contained therein.

The added amount of water is preferably from 300.0 to 3000.0 parts by mass, more preferably from 400.0 to 2500.0 parts by mass, still more preferably from 500.0 to 2000.0 parts by mass, and particularly preferably from 600.0 to 1500.0 parts by mass, relative to 100 parts by mass of HPMCAS from the standpoint of efficiency of the coating.

The enteric coating composition may further comprise an optional plasticizer and/or an optional neutralizer.

Examples of the plasticizer include higher alcohols (alcohols having preferably 6 to 22 carbon atoms), polyhydric alcohols (alcohols having preferably 2 to 6 valences), alkylene glycols, trialkyl citrates, acylglycerols, polyoxyethylene sorbitan fatty acid esters, dibutyl sebacate, and bead waxes. The optional plasticizer may be used singly or in combination of two or more.

Examples of the higher alcohols include cetanol and stearyl alcohol.

Examples of the polyhydric alcohols include glycerin.

Examples of the alkylene glycols include polyethylene glycol and propylene glycol.

Examples of the trialkyl citrates include triethyl citrate and tributyl citrate.

Examples of the acylglycerols include monoacylglycerols such as glycerin monoacetate and glycerin monostearate, and triacylglycerols such as triacetin.

Examples of the polyoxyethylene sorbitan fatty acid esters include polysorbates such as polyoxyethylene sorbitan monolaurate (polysorbate 20), polyoxyethylene sorbitan monostearate (polysorbate 60), and polyoxyethylene sorbitan monooleate (polysorbate 80).

The plasticizer is preferably triethyl citrate, propylene glycol, glycerin monoacetate, or triacetin from the standpoint of the film-forming property.

The amount of the plasticizer to be added is preferably 35 parts by mass or less, more preferably 30 parts by mass or less, still more preferably 28 parts by mass or less, and particularly preferably 25 parts by mass or less, relative to 100 parts by mass of the HPMCAS from the standpoint of maintaining the strength and acid resistance of the film and reducing agglomeration in the aqueous dispersion. In addition, it is preferably 2 parts by mass or more, more preferably 7 parts by mass or more, and still more preferably 15 parts by mass or more, from the standpoint of obtaining uniform coating after dried.

In particular, it has been found that by setting the molar substitution (MS) of hydroxypropoxy groups of 0.40 or more, a film can be formed at a lower temperature even at the same amount as the conventional amount. The above-described HPMCAS may be used regardless of the presence or absence of a plasticizer. For example, regarding the HPMCAS, the preferred range of each of the molar substitution (MS) of hydroxypropoxy groups, the degree of substitution (DS) of methoxy groups, the degree of substitution (DS) of acetyl groups, the degree of substitution (DS) of succninyl groups, the ratio of the degree of substitution of acetyl groups to the molar substitution of hydroxypropoxy groups, the ratio of the degree of substitution of acetyl groups to the degree of substitution of succinyl groups, the preferred ranges of the viscosity, and the preferred ranges of the volume-average particle size are the same as those described above regardless of the presence or absence of a plasticizer. When a plasticizer is present, the ratio of the smallest mass percent "P(%)" of the plasticizer required for forming a film at 25° C. relative to the amount of HPMCAS to the ratio "Ac/Suc" of the degree of substitution of acetyl groups to the degree of substitution of succinyl groups, that is, the ratio of "P/(Ac/Suc)" is preferably greater than 0 and not more than 8.00, more preferably 1.00 to 6.00. The ratio "Ac/Suc" is useful as an index of film formability, and when the degree of substitution of acetyl groups is larger and/or the degree of substitution of succinyl groups is smaller, film formation tends to become difficult. When the ratio "Ac/Suc" is large and it is difficult to form a film, it is preferable to add a plasticizer having a film-forming property and to select the value of "P/(Ac/Suc)" within the above range.

Examples of the neutralizer include basic substances such as ammonia, monoethanolamine, sodium hydroxide, and arginine. The optional neutralizer may be used singly or in combination of two or more. The neutralizer is preferably ammonia from the standpoint of a lower amount of residue due to evaporation during drying in the production of a solid preparation.

The neutralizer may be dissolved in a solvent such as water and used as a solution, if necessary.

The amount of the neutralizer is preferably 0.01 to 5.00 parts by mass, more preferably 1.50 to 4.00 parts by mass, relative to 100 parts by mass of HPMCAS from the standpoint of the operability of coating.

When the neutralizer is used as a solution, the amount of the neutralizer contained in the solution may be selected to fall within the above-mentioned range.

The enteric coating composition may comprise an optional additive in an amount commonly used in the art. Examples of the additive are various and include a lubricant, the other coating base material, a surfactant, a sweetener, a pigment, and an antifoaming agent. The optional additive may be used singly or in combination of two or more.

Examples of the lubricant include talc, magnesium stearate, calcium stearate, colloidal silica, stearic acid, and fumed silica. It is preferably talc from the standpoint of preventing adhesion between HPMCAS particles during coating.

The amount of the lubricant to be added to the enteric coating composition is not particularly limited as long as it does not deteriorate acid resistance. It is preferably 200.0 parts by mass or less, more preferably 0.1 to 100.0 parts by mass relative to the 100 parts by mass of the HPMCAS.

The other coating base material is a coating base material other than the enteric base material HPMCAS. Examples of the other coating base material include water-soluble polyvinyl derivatives such as polyvinyl pyrrolidone and polyvinyl alcohol; water-insoluble cellulose ethers such as ethyl cellulose and hypromellose phthalate; and acrylic copolymers such as a methacrylic acid copolymer LD and an ethyl acrylate-methyl methacrylate copolymer.

The amount of the other coating base material to be added is preferably 100.0 parts by mass or less, more preferably 0.1 to 50.0 parts by mass, relative to 100 parts by mass of the HPMCAS from the standpoint of acid resistance.

Examples of the surfactant include anionic surfactants such as sodium alkyl sulfates (e.g. sodium lauryl sulfate and dioctyl sodium sulfosuccinate), fatty acid sodium (e.g. sodium oleate), and fatty acid potassium (e.g. potassium sorbate); polysorbate 80; cured oils; polyoxyethylene (105) polyoxypropylene (5) glycol (PEP101); and polyoxyethylene (160) polyoxypropylene (30) glycol. The surfactant is preferably an alkali metal salt of alkyl sulfate such as sodium lauryl sulfate from the standpoint of acid resistance.

The amount of the surfactant to be added is not particularly limited as long as it does not hinder the effects of the invention. It is preferably 30 parts by mass or less, more preferably 1 to 10 parts by mass, and still more preferably 2 to 5 parts by mass relative to 100 parts by mass of the HPMCAS from the standpoint of suppressing the generation of agglomerates of the HPMCAS.

Examples of the sweetener include monosaccharides and disaccharides such as glucose, fructose, sucrose, lactose, paratinose, trehalose and xylose; isomerized sugars such as a glucose fructose liquid sugar and a fructose glucose liquid sugar; sugar alcohols such as erythritol, xylitol, lactitol, Palatinit, sorbitol and reduced sugar syrup; and high-intensity sweeteners such as sucralose, acesulfame potassium, thaumatin, aspartame; and honey.

The amount of the sweetener to be added is preferably 0.1 to 50.0 parts by mass relative to 100 parts by mass of the HPMCAS from the standpoint of improving the taste while maintaining the strength and acid resistance of the film.

Examples of the pigment include rutile titanium dioxide, anatase titanium dioxide, white lead, basic lead sulfate, basic lead silicate, zinc oxide, zinc sulfide, and antimony trioxide.

The amount of the pigment to be added is preferably 0.1 to 50.0 parts by mass relative to 100 parts by mass of the HPMCAS from the standpoint of coloring while maintaining the strength and acid resistance of the film.

Examples of the antifoaming agent include glycerol fatty acid esters, dimethylpolysiloxane, dimethylpolysiloxane-silicon dioxide mixtures, hydrated silica, and silicon dioxide.

The amount of the antifoaming agent to be added is preferably 0.1 to 50.0 parts by mass relative to 100 parts by mass of the HPMCAS from the standpoint of defoaming the film while maintaining the strength and acid resistance of the film.

The enteric coating composition may be produced by a method comprising a step of mixing the HPMCAS with water to obtain the enteric coating composition.

Regarding mixing of the HPMCAS with water, the HPMCAS may be added to water, or water may be added to the HPMCAS. The HPMCAS is preferably added to water from the standpoint of dispersibility of the HPMCAS.

The additions of the plasticizer, the neutralizer and the additive are not particularly limited. For example, the HPMCAS may be added to a mixture of water, the plasticizer, the neutralizing agent and the additive. In another example, the HPMCAS may be mixed with water, and then subjected to addition of the plasticizer, the neutralizer and the additive. From the standpoint of reducing the agglomeration of the HPMCAS and improving the dispersibility, the water may be first mixed with a surfactant as the plasticizer and/or additive.

The mixing of the HPMCAS with the water may be carried out, for example, by a stirrer or a disperser.

Examples of the stirrer include a propeller stirrer. The rotational speed of the stirrer is preferably 100 rpm to 1000 rpm from the standpoint of preventing agglomeration of the HPMCAS caused by generation of bubbles.

Examples of the disperser include a disperser for applying a high shear force such as a homogenizer and a bead mill. The dispenser allows the HPMCAS to be mixed with water while dispersing the HPMCAS into fine pieces. The number of rotations in the disperser is preferably 1000 to 10000 rpm for a homogenizer and preferably 1000 to 10000 rpm for a bead mill, from the standpoint of dispersing into fine pieces.

The temperature for producing the enteric coating composition may be appropriately selected. It is preferably 5 to 30° C., more preferably 5 to 25° C., from the standpoint of convenience of the production.

The mixing time for producing the enteric coating composition is preferably from 5 to 60 minutes after adding all of the HPMCAS, water, an optional plasticizer, an optional neutralizer and an optional additive, from the standpoint of sufficiently dispersing the HPMCAS in the water and thoroughly mixing the HPMCAS with the optional plasticizer, neutralizer and/or additive.

Next, a solid preparation coated with the enteric coating composition will be described. The solid preparation comprises a drug-containing core and a coating layer directly or indirectly on the core, the coating layer comprising the HPMCAS having a molar substitution of hydropropoxy groups of 0.40 or more. The coating layer indirectly on the core indicates that another layer or layers may be present between the coating layer and the core.

The solid preparation comprising a coating layer comprising the HPMCAS, in other words, an enteric preparation comprising a coating film comprising the HPMCAS, is a preparation in which a drug-containing core is coated with and encapsulated in the enteric coating composition to prevent decomposition and deactivation of the drug in the stomach and reduce the irritant action of the drug on the stomach.

Examples of the enteric preparation include an enteric tablet, an enteric-coated capsule preparation, an enteric granule and a capsule filled with enteric granules, which are described in the Japanese Pharmacopoeia 17th Edition.

The amount of the coating layer containing the HPMCAS in the solid preparation varies, for example, depending on the type, shape, size and surface conditions of the core containing the drug, and the nature of the drug and the additive contained in the core. The amount of the coating layer in the tablet is preferably 2 to 100 parts by mass, more preferably 4 to 12 parts by mass relative to 100 parts by mass of the drug-containing core, and the amount of the coating layer in the fine granule or granule is preferably 3 to 100 parts by mass, more preferably 10 to 30 parts by mass relative to 100 parts by mass of the drug-containing core, from the standpoint of giving a sufficient lag time and allowing the coating to dissolve sufficiently in the intestines.

Next, there will be described a method for producing the solid preparation comprising steps of coating the drug-containing core with the enteric coating composition to obtain a coating layer, and drying the coating layer.

The drug is not particularly limited as long as it is an orally administerable drug. Examples of the drug include a drug for the central nervous system, a drug for the cardiovascular system, a drug for the respiratory system, a drug for the digestive system, an antibiotic, an antitussive and expectorant, an antihistamine, an antipyretic anti-inflammatory analgesic, a diuretic, an autonomic agent, an antimalarial agent, an antidiarrheal agent, a psychotropic, and vitamins and derivatives thereof.

Examples of the drug for the central nervous system include diazepam, idebenone, paracetamol, naproxen, piroxicam, indomethacin, sulindac, lorazepam, nitrazepam, phenytoin, acetaminophen, ethenzamide, and chlordiazepoxide.

Examples of the drug for the cardiovascular system include molsidomine, vinpocetine, propranolol, methyldopa, dipyridamole, furosemide, triamterene, nifedipine, atenolol, spironolactone, metoprolol, pindolol, captopril, isosorbide dinitrate, delapril hydrochloride, meclofenoxate hydrochloride, diltiazem hydrochloride, etilefrine hydrochloride, digitoxin, and alprenolol hydrochloride.

Examples of the drug for the respiratory system include amlexanox, dextromethorphan, theophylline, pseudoephedrine, salbutamol, and guaifenesin.

Examples of the drug for the digestive system include a benzimidazole drug having antiulcer action, such as 2-[[3-methyl-4-(2,2,2-trifluoroethoxy)-2-pyridyl]methylsulfinyl] benzimidazole and 5-methoxy-2-[(4-methoxy-3,5-dimethyl-2-pyridyl)methylsufinyl]benzimidazole; cimetidine; ranitidine; pirenezepine hydrochloride; pancreatin; bisacodyl; and 5-aminosalicylic acid.

Examples of the antibiotic include talampicillin hydrochloride, bacampicillin hydrochloride, cefaclor, and erythromycin.

Examples of the antitussive and expectorant include noscapine hydrochloride, carbetapentane citrate, isoaminile citrate, and dimemorfan phosphate.

Examples of the antihistamine include chlorpheniramine maleate, diphenhydramine hydrochloride, and promethazine hydrochloride.

Examples of the antipyretic anti-inflammatory analgesic include ibuprofen, diclofenac sodium, flufenamic acid, sulpyrine, aspirin, and ketoprofen.

Examples of the diuretic include caffeine.

Examples of the autonomic agent include dihydrocodeine phosphate, dl-methylephedrine hydrochloride, atropine sulfate, acetylcholine chloride, and neostigmine.

Examples of the antimalarial agent include quinine hydrochloride.

Examples of the antidiarrheal agent include loperamide hydrochloride.

Examples of the psychotropic include chlorpromazine.

Examples of the vitamins and derivatives thereof include vitamin A, vitamin B1, fursultiamine, vitamin B2, vitamin B6, vitamin B12, vitamin C, vitamin D, vitamin E, vitamin K, calcium pantothenate, and tranexamic acid.

The drug-containing core may comprise an optional various additive commonly usable in the field, such as an excipient, a binder, a disintegrant, a lubricant, an aggregation inhibitor, and a solubilizing agent for a pharmaceutical compound. The content of the additive may be appropriately selected depending on the type of the drug or the like.

Examples of the excipient include a saccharide such as white soft sugar, lactose, mannitol and glucose; starch; crystalline cellulose; calcium phosphate; and calcium sulfate.

Examples of the binder include polyvinyl alcohol, polyacrylic acid, polymethacrylic acid, polyvinylpyrrolidone, glucose, white soft sugar, lactose, maltose, dextrin, sorbitol, mannitol, hydroxyethyl cellulose, hydroxypropyl methyl cellulose, hydroxypropyl cellulose, macrogols, gum arabic, gelatin, agar, and starch.

Examples of the disintegrant include low-substituted hydroxypropyl cellulose, carmellose or a salt thereof, croscarmellose sodium, sodium carboxymethyl starch, crospovidone, crystalline cellulose, and crystalline cellulose-carmellose sodium.

Examples of the lubricant and the aggregation inhibitor include talc, magnesium stearate, calcium stearate, colloidal silica, stearic acid, waxes, hardened oil, polyethylene glycol, and sodium benzoate.

Examples of the solubilizing agent for a pharmaceutical compound include organic acids such as fumaric acid, succinic acid, malic acid and adipic acid.

The shape (dosage form) of the drug-containing core is not particularly limited. Examples of the dosage form include tablets; pills; and non-enteric capsules, granules, powder, and the like produced by using gelatine, HPMC or the like.

The coating with the enteric coating composition may be carried out by a known method such as spray coating with a coating apparatus. Examples of the coating apparatus include a pan coating apparatus, a drum type coating apparatus, a fluidized bed coating apparatus, a stirred flow coating apparatus, and a rolling flow coating apparatus. Any of air spray, airless spray, three-fluid spray and the like may be used as a spray accompanied by the coating apparatus.

The temperature at which the enteric coating composition is fed to the coating apparatus may be appropriately selected. It is preferably 5 to 30° C., more preferably 5 to 25° C., and still more preferably 5 to 10° C., from the standpoint of liquid feeding performance and convenience. Since the enteric coating composition contains none or a reduced amount of plasticizer, it is possible to avoid or reduce the occurrence of nozzle blockage during coating.

The drying is not particularly limited as long as water can be removed. The drying may be carried out, for example, by heating a target in the coating apparatus or after being taken out of the coating apparatus.

The temperature of blowing air to be used for drying is preferably 25 to 90° C. from the standpoint of drying the coating layer at a sufficient speed while keeping the drug-containing core at a desired level of moisture.

EXAMPLES

The invention will be explained based on Examples and Comparative Examples. It should not be construed that the invention is limited to these examples.

<Synthesis of HPMCAS-1>

The 960 g of glacial acetic acid was weighed into a 5 L kneader, and then 600 g of hypromellose (HPMC) having a molar substitution of hydroxypropoxy groups of 0.45 and a degree of substitution of methoxy groups of 1.82 was added thereto and dissolved. Further, 371 g of acetic anhydride, 81 g of succinic anhydride and 260 g of sodium acetate were added thereto, and the reaction was carried out at 85° C. for 5 hours. After 670 g of purified water was added to the reaction product mixture and stirred, purified water was further added to the reaction product mixture to obtain a suspension in which HPMCAS was precipitated. After filtering the suspension to obtain crude HPMCAS, the crude HPMCAS was washed with purified water, dried, and sieved through a 10-mesh sieve (opening: 1700 micrometers) to obtain HPMCAS.

The obtained HPMCAS was pulverized to obtain HPMCAS-1. The pulverization was carried out using a LJ-K1 (jet mill, Nippon Pneumatic Mfg. Co., Ltd.) under the following conditions: a feed rate of 2.0 g/min, a nozzle pressure of 0.4 MPa, no distance ring, and the louver size of "small".

A molar substitution of hydroxypropoxy groups, a degree of substitution of the methoxy groups, a degree of substitution of acetyl groups and a degree of substitution of succinyl groups of the resulting HPMCAS-1, a viscosity at 20° C. of the 2% by weight HPMCAS-1 solution in a dilute sodium hydroxide aqueous solution (a sodium hydroxide concentration of 0.1 mol/L), and the particle sizes ($D_{10}$, $D_{50}$ and $D_{90}$)) of HPMCAS-1 are shown in Table 2. The particle sizes ($D_{10}$, $D_{50}$ and $D_{90}$) of the HPMCAS-1 were measured at a dispersing pressure of 2 bars by using a dry laser diffraction particle size distribution measuring device (Mastersizer 3000, product of Malvern Corporation).

<Synthesis of HPMCAS-2 to 8>

HPMCAS-2 to 8 shown in Table 2 were obtained in the same manner as in production of HPMCAS-1 except for using HPMC having different degrees of substitutions, appropriately changing the amounts of acetic anhydride and succinic anhydride, and/or changing the pulverization mode.

Each of HPMCAS-2, 3, 5, 6 and 8 was produced by pulverizing the obtained HPMCAS under the same pulverization conditions as those for the HPMCAS-1 using a jet mill LJ-K1.

Each of HPMCAS-4 and 7 was produced by pulverizing the obtained HPMCAS under the same pulverization conditions as those for HPMCAS-1 using a jet mill LJ-K1 except that the classification point was changed by setting the louver size to "large".

TABLE 2

| HPMCAS | substitution degree | | | | | | viscosity | particle size | | |
|---|---|---|---|---|---|---|---|---|---|---|
| | HPO | MeO | Ac | Suc | Ac/HPO | Ac/Suc | (mPa·s) | $D_{10}$ (μm) | $D_{50}$ (μm) | $D_{90}$ (μm) |
| HPMCAS-1 | 0.45 | 1.82 | 0.69 | 0.19 | 1.53 | 3.63 | 2.78 | 1.2 | 6 | 11 |
| HPMCAS-2 | 0.59 | 1.57 | 0.55 | 0.34 | 0.93 | 1.62 | 2.69 | 0.8 | 4 | 8 |
| HPMCAS-3 | 0.61 | 1.84 | 0.52 | 0.32 | 0.85 | 1.63 | 3.14 | 1.2 | 6 | 11 |
| HPMCAS-4 | 0.61 | 1.84 | 0.47 | 0.41 | 0.77 | 1.15 | 2.95 | 2.1 | 9 | 18 |
| HPMCAS-5 | 0.63 | 1.82 | 0.68 | 0.22 | 1.08 | 3.09 | 2.75 | 1.2 | 6 | 11 |
| HPMCAS-6 | 0.63 | 1.82 | 0.59 | 0.29 | 0.94 | 2.03 | 2.72 | 1.4 | 7 | 13 |
| HPMCAS-7 | 0.84 | 1.58 | 0.82 | 0.20 | 0.98 | 4.10 | 3.12 | 2.3 | 10 | 20 |
| HPMCAS-8 | 0.25 | 1.90 | 0.67 | 0.19 | 2.68 | 3.53 | 2.86 | 0.9 | 5 | 11 |

* In Table 2, HPO means hydroxypropoxy, MeO means methoxy, Ac means acetyl, and Suc means succinyl.

(1) Enteric Coating Composition Containing No Plasticizer

Examples 1 to 5 and Comparative Example 1

Pure water (1325.6 parts by mass) was added into a 200 ml beaker, and stirred at 200 rpm using a propeller stirrer (NZ-1100, product of Tokyo Rikakikai Co., Ltd.) while being cooled to about 10° C. in an ice bath. Next, while cooling to about 10° C., sodium lauryl sulfate (SLS) (3 parts by mass) as a surfactant was added thereto and mixed, and then HPMCAS (100 parts by mass) selected from HPMCAS-2 to 4 and 6 to 8 was added thereto, followed by stirring at 200 rpm for 30 minutes while cooling to about 10° C. to produce an enteric coating composition which was an aqueous dispersion of HPMCAS.

In order to evaluate the coating performance (film-forming property) of each enteric coating composition produced, film formation on a glass plate was tested. The 100 μl aliquots of the enteric coating composition were cast on five glass plates, and dried in an oven at each temperature (25, 30, 40, 50 or 60° C.) for 2 hours to visually inspect the film formation. The lowest drying temperature at which a transparent film was formed over the whole of each of the five plates was determined as the "film formation temperature". The results are shown in Table 3.

Examples 6 to 8 and Comparative Example 2

Pure water (1323.0 parts by mass) was added into a 200-mL beaker at room temperature, and then sodium lauryl sulfate (SLS) (3 parts by mass) as a surfactant was added thereto and mixed while stirring at 200 rpm using a propeller stirrer (NZ-1100, product of Tokyo Rikakikai Co., Ltd.). Next, HPMCAS-1, 3, 5 or 8 (100 parts by mass) was added thereto, and stirred at 200 rpm at room temperature to produce an aqueous dispersion. Then, 10% by mass of an aqueous ammonia solution (2.60 parts by mass in terms of ammonia) was added thereto and stirred at 200 rpm for 30 minutes at room temperature to produce an enteric coating composition which was an aqueous dispersion of partially neutralized HPMCAS.

In order to evaluate the coating performance (film-forming property) of each enteric coating composition produced, film formation on a glass plate was tested in the same manner as in Examples 1 to 5. The results are shown in Table 3.

TABLE 3

| | HPMCAS | substitution degree | | | | | | viscosity | particle size | | | neutralizer | film formation temperature (° C.) |
|---|---|---|---|---|---|---|---|---|---|---|---|---|---|
| | | HPO | MeO | Ac | Suc | Ac/HPO | Ac/Suc | (mPa·s) | $D_{10}$ (μm) | $D_{50}$ (μm) | $D_{90}$ (μm) | | |
| Example1 | HPMCAS-2 | 0.59 | 1.57 | 0.55 | 0.34 | 0.93 | 1.62 | 2.69 | 0.8 | 4 | 8 | none | 40 |
| Example2 | HPMCAS-3 | 0.61 | 1.84 | 0.52 | 0.32 | 0.85 | 1.63 | 3.14 | 1.2 | 6 | 11 | none | 40 |
| Example3 | HPMCAS-4 | 0.61 | 1.84 | 0.47 | 0.41 | 0.77 | 1.15 | 2.95 | 2.1 | 9 | 18 | none | 40 |
| Example4 | HPMCAS-6 | 0.63 | 1.82 | 0.59 | 0.29 | 0.94 | 2.03 | 2.72 | 1.4 | 7 | 13 | none | 60 |
| Example5 | HPMCAS-7 | 0.84 | 1.58 | 0.82 | 0.20 | 0.98 | 4.10 | 3.12 | 2.3 | 10 | 20 | none | 40 |
| Comp. Ex. 1 | HPMCAS-8 | 0.25 | 1.90 | 0.67 | 0.19 | 2.68 | 3.53 | 2.86 | 0.9 | 5 | 11 | none | unable |
| Example6 | HPMCAS-1 | 0.45 | 1.82 | 0.69 | 0.19 | 1.53 | 3.63 | 2.78 | 1.2 | 6 | 11 | aqueous ammonia | 60 |
| Example7 | HPMCAS-3 | 0.61 | 1.84 | 0.52 | 0.32 | 0.85 | 1.63 | 3.14 | 1.2 | 6 | 11 | aqueous ammonia | 30 |
| Example8 | HPMCAS-5 | 0.63 | 1.82 | 0.68 | 0.22 | 1.08 | 3.09 | 2.75 | 1.2 | 6 | 11 | aqueous ammonia | 50 |
| Comp. Ex. 2 | HPMCAS-8 | 0.25 | 1.90 | 0.67 | 0.19 | 2.68 | 3.53 | 2.86 | 0.9 | 5 | 11 | aqueous ammonia | unable |

* In Table 3, HPO means hydroxypropoxy, MeO means methoxy, Ac means acetyl, and Suc means succinyl.

It is evident from the results of Examples 1 to 5 that when HPMCAS has a molar substitution of hydroxypropoxy groups of 0.4 or more, a film could be formed at a lower temperature without using a plasticizer.

Further, it is evident from the results of Examples 6 to 8 that the same effects can be obtained even when a neutralizer is used.

(2) Enteric Coating Composition Containing a Plasticizer at an Amount Smaller than the Conventional Amount.

Examples 9 to 17 and Comparative Examples 3 to 5

Pure water was added into a 200-mL beaker. While cooled to about 10° C. in an ice bath, a plasticizer was added thereto and mixed with stirring at 200 rpm using a propeller stirrer (NZ-1100, product of Tokyo Rikakikai Co., Ltd.). Next, while cooling to about 10° C., sodium lauryl sulfate (SLS) (3 parts by mass) as a surfactant was added thereto and mixed, and then HPMCAS (100 parts by mass) selected from HPMCAS-1 to 8 was added thereto and stirred at 200° C. for 30 minutes while cooling to about 10° C., thereby producing an enteric coating composition which was an aqueous dispersion having the different plasticizer content relative to HPMCAS. The enteric coating composition was classified into composition types A to C depending on the plasticizer content, and the composition of each type is shown in Table 4.

In order to evaluate the coating performance (film-forming property) of each enteric coating composition produced, film formation on a glass plate was tested. The 100 µl aliquots of the enteric coating composition were cast on five glass plates, and dried in an oven at each temperature (25, 30, 40, 50 or 60° C.) for 2 hours to visually inspect the film formation. The lowest drying temperature at which a transparent film was formed over the whole on each of the five plates was determined as the film formation temperature. The results are shown in Tables 5 and 6.

Examples 18 to 20 and Comparative Example 6

Pure water was added into a 200-mL beaker at room temperature, and then sodium lauryl sulfate (SLS) (3 parts by mas) as a surfactant was added thereto and mixed with stirring at 200 rpm using a propeller stirrer (NZ-1100, product of Tokyo Rikakikai Co., Ltd.). Next, HPMCAS-1, 3, 5 or 8 (100 parts by mass) was added thereto and stirred at 200 rpm at room temperature to produce an aqueous dispersion. Then, a 10% by mass aqueous ammonia solution ($NH_3$(aq)) (2.60 parts by mass in terms of ammonia) was added thereto, and stirred at 200 rpm at room temperature. A plasticizer was added thereto, and stirred at 200 rpm for 30 minutes at room temperature to produce an enteric coating composition which was an aqueous dispersion having a different plasticizer content relative to the partially neutralized HPMCAS, as shown in Table 4. The enteric coating composition was classified into types D-E depending on the plasticizer content and the composition of each type is shown in Table 4.

In order to evaluate the coating performance (film-forming property) of each enteric coating composition produced, film formation on a glass plate was tested in the same manner as in Examples 1 to 6. The results are shown in Tables 5 and 6.

TABLE 4

| | enteric coating composition | | | | |
|---|---|---|---|---|---|
| | plasticizer (pbm) | HPMCAS (Pbm) | water (Pbm) | surfactant (Pbm) | neutralizer (pbm: parts by mass) |
| Composition Type A | 5 | 100 | 1320.6 | 3 | none |
| Composition Type B | 10 | 100 | 1315.6 | 3 | none |
| Composition Type C | 20 | 100 | 1305.6 | 3 | none |
| Composition Type D | 30 | 100 | 1295.6 | 3 | none |
| Composition Type E | 5 | 100 | 1318.0 | 3 | 2.60 |
| Composition Type F | 10 | 100 | 1313.0 | 3 | 2.60 |
| Composition Type G | 20 | 100 | 1303.0 | 3 | 2.60 |
| Composition Type H | 30 | 100 | 1293.0 | 3 | 2.60 |

TABLE 5

| | HPMCAS | substitution degree | | | | | | viscosity (mPa·s) | particle size | | | plasticizer | neutralizer |
| | | HPO | MeO | Ac | Suc | Ac/HPO | Ac/Suc | | $D_{10}$ (µm) | $D_{50}$ (µm) | $D_{90}$ (µm) | | |
|---|---|---|---|---|---|---|---|---|---|---|---|---|---|
| Example9 | HPMCAS-1 | 0.45 | 1.82 | 0.69 | 0.19 | 1.53 | 3.63 | 2.78 | 1.2 | 6 | 11 | TEC | none |
| Example10 | HPMCAS-1 | 0.45 | 1.82 | 0.69 | 0.19 | 1.53 | 3.63 | 2.78 | 1.2 | 6 | 11 | TA | none |
| Example11 | HPMCAS-2 | 0.59 | 1.57 | 0.55 | 0.34 | 0.93 | 1.62 | 2.69 | 0.8 | 4 | 8 | TEC | none |
| Example12 | HPMCAS-3 | 0.61 | 1.84 | 0.52 | 0.32 | 0.85 | 1.63 | 3.14 | 1.2 | 6 | 11 | TEC | none |
| Example13 | HPMCAS-4 | 0.61 | 1.84 | 0.47 | 0.41 | 0.77 | 1.15 | 2.95 | 2.1 | 9 | 18 | TEC | none |
| Example14 | HPMCAS-5 | 0.63 | 1.82 | 0.68 | 0.22 | 1.08 | 3.09 | 2.75 | 1.2 | 6 | 11 | TEC | none |
| Example15 | HPMCAS-6 | 0.63 | 1.82 | 0.59 | 0.29 | 0.94 | 2.03 | 2.72 | 1.4 | 7 | 13 | TEC | none |
| Example16 | HPMCAS-6 | 0.63 | 1.82 | 0.59 | 0.29 | 0.94 | 2.03 | 2.72 | 1.4 | 7 | 13 | PG | none |
| Example17 | HPMCAS-7 | 0.84 | 1.58 | 0.82 | 0.20 | 0.98 | 4.10 | 3.12 | 2.3 | 10 | 20 | TEC | none |
| Comp. Ex. 3 | HPMCAS-8 | 0.25 | 1.90 | 0.67 | 0.19 | 2.68 | 3.53 | 2.86 | 0.9 | 5 | 11 | TEC | none |
| Comp. Ex. 4 | HPMCAS-8 | 0.25 | 1.90 | 0.67 | 0.19 | 2.68 | 3.53 | 2.86 | 0.9 | 5 | 11 | TA | none |
| Comp. Ex. 5 | HPMCAS-8 | 0.25 | 1.90 | 0.67 | 0.19 | 2.68 | 3.53 | 2.86 | 0.9 | 5 | 11 | PG | none |
| Example18 | HPMCAS-1 | 0.45 | 1.82 | 0.69 | 0.19 | 1.53 | 3.63 | 2.78 | 1.2 | 6 | 11 | TEC | $NH_3$(aq) |
| Example19 | HPMCAS-3 | 0.61 | 1.84 | 0.52 | 0.32 | 0.85 | 1.63 | 3.14 | 1.2 | 6 | 11 | TEC | $NH_3$(aq) |
| Example20 | HPMCAS-5 | 0.63 | 1.82 | 0.68 | 0.22 | 1.08 | 3.09 | 2.75 | 1.2 | 6 | 11 | TEC | $NH_3$(aq) |
| Comp. Ex. 6 | HPMCAS-8 | 0.25 | 1.90 | 0.67 | 0.19 | 2.68 | 3.53 | 2.86 | 0.9 | 5 | 11 | TEC | $NH_3$(aq) |

* In Table 5, HPO means hydroxypropoxy, MeO means methoxy, Ac means acetyl, Suc means succinyl, TEC means triethyl citrate, TA means triacetin, and PG means propylene glycol.

TABLE 6

| | evaluation results | | | | | | | | | |
|---|---|---|---|---|---|---|---|---|---|---|
| | film formation temperature of Composition Types A to E | | | | | | | | minimum mass percentage P of plasticizer required to form film at 25° C., relative to HPMCAS | P/(Ac/Suc) |
| | A (° C.) | B (° C.) | C (° C.) | D (° C.) | E (° C.) | F (° C.) | G (° C.) | H (° C.) | | |
| Example9 | 50 | 30 | 25 | 25 | — | — | — | — | 20 | 5.51 |
| Example10 | 40 | 30 | 25 | 25 | — | — | — | — | 20 | 5.51 |
| Example11 | 25 | 25 | 25 | 25 | — | — | — | — | 5 | 3.09 |
| Example12 | 25 | 25 | 25 | 25 | — | — | — | — | 5 | 3.07 |
| Example13 | 25 | 25 | 25 | 25 | — | — | — | — | 5 | 4.35 |
| Example14 | 40 | 25 | 25 | 25 | — | — | — | — | 10 | 3.24 |
| Example15 | 40 | 25 | 25 | 25 | — | — | — | — | 10 | 4.93 |
| Example16 | 50 | 25 | 25 | 25 | — | — | — | — | 10 | 4.93 |
| Example17 | 25 | 25 | 25 | 25 | — | — | — | — | 5 | 1.22 |
| Comp. Ex. 3 | unable | 60 | 40 | 25 | — | — | — | — | 30 | 8.50 |
| Comp. Ex. 4 | unable | 60 | 30 | 25 | — | — | — | — | 30 | 8.50 |
| Comp. Ex. 5 | unable | unable | unable | unable | — | — | — | — | unable | >8.50 |
| Example18 | — | — | — | — | 40 | 25 | 25 | 25 | 10 | 2.75 |
| Example19 | — | — | — | — | 25 | 25 | 25 | 25 | 5 | 3.07 |
| Example20 | — | — | — | — | 30 | 25 | 25 | 25 | 10 | 3.24 |
| Comp. Ex. 6 | — | — | — | — | unable | 50 | 30 | 25 | 30 | 8.50 |

* In Table 6, Ac means acetyl, and Suc means succinyl.

It is evident from the results of Examples 9 to 10 and Comparative Examples 3 to 4 where each HPMCAS having the same amounts of acetyl groups and succinyl groups and the same particle size was used, that when HPMCAS having a molar substitution of hydroxypropoxy groups of 0.40 or more was used, the film can be formed in a smaller amount of plasticizer at a lower temperature.

It is also evident from the results of Examples 11 to 17 and Comparative Example 5 that the same effects are confirmed even when HPMCAS having various degrees of substitution and a plasticizer are used.

It is further evident from the results of Examples 18 to 20 and Comparative Example 6 that the same effects are confirmed even when a neutralizer is used. In particular, when a neutralizer and a plasticizer were used in combination, a film could be formed at a lower temperature than when only a plasticizer was used. It is considered that the hydrophilicity of the hydroxypropoxy groups improved the affinity between HPMCAS and water, and the HPMCAS was melted in the drying step, and consequently, the film was formed.

Furthermore, it is found that the values of "P/(Ac/Suc)" are lower in Examples in comparison with the results in Examples and Comparative Examples in which the same type of plasticizers were used.

The invention claimed is:

1. An enteric coating composition comprising: hypromellose acetate succinate having a molar substitution of hydroxypropoxy groups from 0.40 to 0.85, a ratio of a degree of substitution of acetyl groups to the molar substitution of hydroxypropoxy groups from 0.70 to 1.60, and a degree of substitution of succinyl groups of from 0.15 to 0.45, and water.

2. The enteric coating composition according to claim 1, wherein the hypromellose acetate succinate has a volume-average particle size ($D_{50}$) of 30 μm or less.

3. The enteric coating composition according to claim 1, further comprising a plasticizer and/or a neutralizer.

4. The enteric coating composition according to claim 3, wherein the plasticizer is at least one selected from the group consisting of higher alcohols, polyhydric alcohols, alkylene glycols, trialkyl citrates, acylglycerols, polyoxyethylene sorbitan fatty acid esters, dibutyl sebacate, and bead waxes.

5. The enteric coating composition according to claim 3, wherein the neutralizer is at least one selected from the group consisting of ammonia, monoethanolamine, sodium hydroxide, and arginine.

6. A method for producing a solid preparation comprising steps of:
coating a drug-containing core with the enteric coating composition according to claim 1 to obtain a coating layer, and
drying the coating layer.

7. A solid preparation comprising:
a core containing a drug, and
a coating layer directly or indirectly on the core, the coating layer comprising hypromellose acetate succinate having a molar substitution of hydroxypropoxy groups from 0.40 to 0.85 a ratio of a degree of substitution of acetyl groups to the molar substitution of hydroxypropoxy groups from 0.70 to 1.60, and a degree of substitution of succinyl groups from 0.15 to 0.45.

\* \* \* \* \*